United States Patent
Pyrozyk et al.

[11] Patent Number: 5,431,622
[45] Date of Patent: Jul. 11, 1995

[54] THERMAL BANDAGE

[75] Inventors: Ronald R. Pyrozyk, Penticton; Steve R. Sharp, Fort McMurray, both of Canada

[73] Assignee: Okanagan House Inc., Penticton, Canada

[21] Appl. No.: 165,570

[22] Filed: Dec. 13, 1993

Related U.S. Application Data

[63] Continuation of Ser. No. 926,438, Aug. 10, 1992, abandoned.

[51] Int. Cl.[6] .......................... A61L 15/00; A61F 7/00
[52] U.S. Cl. .......................................... 602/2; 602/52;
602/54; 602/79; 602/43; 602/41; 602/96;
602/108; 602/114; 602/113
[58] Field of Search .................. 602/2, 41, 42, 43, 48,
602/52, 57, 58, 74, 79, 54; 604/290, 291, 386,
387, 389; 607/96, 108, 109, 112, 114

[56] References Cited

U.S. PATENT DOCUMENTS

| | | | |
|---|---|---|---|
| 2,573,791 | 11/1951 | Howells | 604/291 X |
| 3,175,558 | 3/1965 | Caillouette et al. | 128/403 |
| 3,596,657 | 8/1971 | Eldus | 602/2 |
| 3,780,537 | 12/1973 | Spencer | 128/403 X |
| 3,871,376 | 3/1975 | Kozak | 128/403 X |
| 3,885,403 | 5/1975 | Spencer | 62/530 |
| 4,055,188 | 10/1977 | Pelton | 128/402 |
| 4,081,150 | 3/1978 | Tyson | 128/402 |
| 4,377,160 | 3/1983 | Romaine | 602/2 |
| 4,397,315 | 8/1983 | Patel | 128/402 X |
| 4,586,506 | 5/1986 | Nangle | 128/403 |
| 4,592,358 | 6/1986 | Westplate | 128/402 |
| 4,676,247 | 6/1987 | Van Cleve | 128/402 |
| 4,688,572 | 8/1987 | Hubbard et al. | 128/402 |
| 4,900,319 | 2/1990 | Richwine | 604/386 X |
| 4,908,248 | 3/1990 | Nakashima et al. | 428/355 |
| 4,964,402 | 10/1990 | Grim et al. | 602/2 |
| 4,967,573 | 11/1990 | Wilhelm | 128/402 X |
| 5,088,487 | 2/1992 | Turner | 128/402 |

FOREIGN PATENT DOCUMENTS 0036910  7/1981  European Pat. Off. .

*Primary Examiner*—Richard J. Apley
*Assistant Examiner*—Beverly A. Meindl
*Attorney, Agent, or Firm*—Bull, Housser & Tupper

[57] ABSTRACT

A thermal bandage apparatus for simultaneously dressing and thermally treating a wounded bodily area includes a fluid absorbent member having a wound contacting surface for absorbing bodily fluids produced by an open wound and holding means adjacent and connected to the fluid absorbent member for holding a thermal medium against the fluid absorbent member such that heat is transferred between the thermal medium and the open wound by thermal conduction through the fluid absorbent member. There is also disclosed an arrangement for providing a continuous supply of heat or cold to a wound.

15 Claims, 5 Drawing Sheets

THERMAL BANDAGE

This is a continuation of application Ser. No. 07/926,438 filed Aug. 10, 1992, now abandoned.

This invention relates to bandages and more particularly to bandages which dress a wound while at the same time providing heat or cold to a wound area.

Thermal therapies have been used for many years to treat ailments such as toothaches, headaches, arthritis, bursitis, burns and bleeding. Thermal therapies have included warm or cold water applied directly to a wound, the use of a hot water bottle and more recently to the use of packages of heat retaining gel such as that described in U.S. Pat. No. 3,885,403 to Spencer, issued May 27, 1975.

Various methods of securing heat retaining packages to a body are described in United States Patents such as U.S. Pat. No. 4,676,247 to Van Cleve issued Jun. 30, 1987, U.S. Pat. No. 4,055,188 to Pelton issued Oct. 25, 1977, U.S. Pat. No. 4,688,572 to Hubbard et al. issued Aug. 25, 1987 and U.S. Pat. No. 4,908,248 to Nakashima et al. issued Mar. 13, 1990. While each of the devices described in the above patents effectively holds a heat retaining package to a body part, it would appear that none is capable of being applied directly to an open wound. Each device requires that an open wound first be dressed with a conventional dressing before the thermal wrap can be applied. This can be time consuming and unnecessarily complicated as two different types of bandages must be tended to; the first being the dressing and the second being the thermal bandage.

The present invention eliminates the use of two different bandages as it effectively combines the dressing and the thermal bandage into one. In addition, the present invention provides a multi-unit bandage which is easily dispensed, in a manner which speeds up the process of dressing a wound and applying heat or cold.

SUMMARY OF THE INVENTION

In accordance with one aspect of the invention, there is provided a thermal bandage apparatus for simultaneously dressing and thermally treating a wounded bodily area, the bandage including a fluid absorbent member having a wound contacting surface for absorbing bodily fluids produced by an open wound and holding means adjacent and connected to the fluid absorbent member for holding a thermal medium against the fluid absorbent member such that heat is transferred between the thermal medium and the open wound by thermal conduction through the fluid absorbent member. There is also disclosed an arrangement for providing a continuous supply of heat or cold to a wound.

In accordance with another aspect of the invention, there is provided a multi-unit thermal bandage comprising a first flexible web member, a plurality of pockets along the first flexible web member at spaced apart intervals along the length of the first flexible web member, a plurality of adhesive areas at spaced apart locations along the first flexible member, at least, one adhesive area being located between each of the pockets and a plurality of frangible areas defined at regular intervals along the first flexible member defining units along the first flexible member, each unit including at least one pocket and at least one adhesive area, each unit being separable from the first flexible web at said frangible areas.

In accordance with another aspect of the invention, there is provided a method of dispensing a multi-unit thermal bandage, the method comprising the step of separating a bandage unit comprising a first flexible member having a plurality of pockets and fluid absorbent material thereon at a frangible connection between said bandage unit and a plurality of similar bandage units joined together by frangible connections.

DETAILED DESCRIPTION

Figure 1:
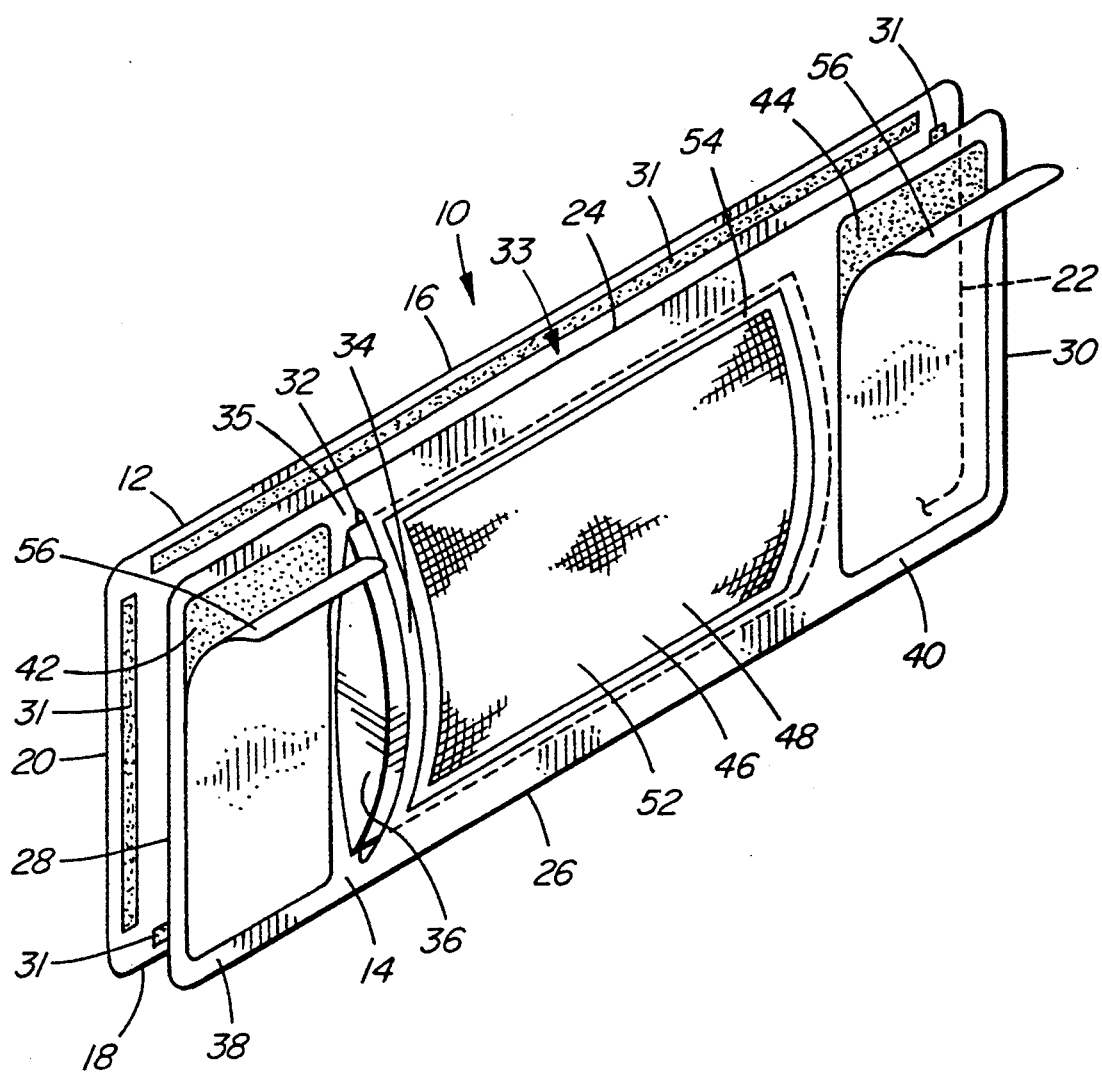
FIG. 1 is an oblique front exploded view of an apparatus according to a first embodiment of the invention.

Referring to FIG. 1, an apparatus according to a first embodiment of the invention is shown generally at 10. The apparatus includes first and second flexible members 12 and 14 each formed of a composite material such as a cotton/fibre mix commonly known as Pellon (Trademark). Other materials will also be acceptable provided they have sufficient strength and pliability to conform to the human body and remain securely attached thereto in accordance with the following.

The first flexible member has first, second, third and fourth edges 16, 18, 20 and 22 while the second member has similar edges 24, 26, 28 and 30. Respective first, second, third and fourth edges of each flexible member are joined together using double sided laminating glue strips 31.

The glue strips 31 are applied to only an approximately ⅛ inch strip along the outer perimeters of the first and second flexible members 12 and 14 and are sandwiched between the edges of the first and second flexible members. Heat is applied to activate the glue to bond the respective edges together. Just the outer perimeter portions of the first and second flexible members are bonded together forming first, second, third and fourth bonded edges. A space 33 is thus formed between the first and second flexible members, in the area between the bonded edges.

To provide access to the space 33, the second flexible member 14 is provided with a transversely extending slit 32 which extends between the first and second bonded edges. A pocket 34 is thus formed, the pocket being bounded by the bonded edge portions and the slit 32, the slit acting as an opening to the pocket. The pocket is therefore approximately the same size as the first and second flexible sheets 12 and 14.

In the embodiment shown, the pocket is of sufficient size to admit a container of a thermal medium such as a conventional hot/cold pack 36 as described in U.S. Pat. No. 3,885,403 to Spencer, issued May 27, 1975. In the embodiment shown, the pocket has a flap 35 formed by one side of the second flexible member adjacent the slit, which acts as closure means for preventing the hot/cold pack 36 from falling out of the pocket.

The second flexible member 14 further includes first and second flexible end portions 38 and 40 having respective first and second adhesive portions 42 and 44 thereon. The first and second adhesive portions face in the same direction when the bandage is laid flat and act as securing means for securing the bandage to body of a person.

Disposed between the first and second end portions 38 and 40 and disposed immediately adjacent the pocket 34 is a fluid absorbent member 46 having a wound facing side 48. The wound facing side has a wound contacting surface 52 thereon, the wound contacting surface facing in the same direction as the first and second adhesive portions 42 and 44. The fluid absorbent member 46 includes conventional cotton fibre batting material sandwiched between first and second sheets of cotton fibre or gauze material and is operable to absorb bodily fluids produced by an open wound.

The fluid absorbent member 46 is secured to a moisture barrier 54 comprised of a fluid impermeable plastic sheet. The moisture barrier is secured to the second flexible member 14 and thereby serves to secure the fluid absorbent member 46 to the second flexible member. The moisture barrier is used to prevent fluids from passing through the fluid absorbent member to the pocket and vice versa.

The second flexible member 14, moisture barrier 54 and fluid absorbent member 46 each have sufficient thermal conductivity to enable the transfer of heat between the hot/cold pack 36 and the wound contacting surface 52.

OPERATION

It is envisaged that the above-described bandage 10 would be shipped in a sterile plastic wrap package (not shown). At the site of treating a wound, the hot/cold pack 36 is preheated or pre-cooled to any desired temperature, using conventional methods. Throughout this discussion, it is to be understood that the terms hot and cold are referenced relative to normal human body temperature.

To use the bandage, one simply removes the plastic packaging (not shown) and inserts the preheated or precooled hot/cold pack 36 into the pocket 34. The adhesive portions 42 and 44 are then exposed by peeling off conventional paper backings 56. The bandage is then handled by third and fourth bonded edges (20, 28 and 22, 30) to place the wound contacting surface 52 against the wound. The first and second adhesive portions 42 and 44 are then pressed against the skin adjacent the wound to secure the bandage in place.

When in place, the bandage allows the fluid absorbent member 46 to absorb any fluids produced by the wound and such fluids are confined to the fluid absorbent member by the moisture barrier 54. At the same time, heat or cold is applied to the wound due to the hot/cold pack 36 being located immediately adjacent the fluid absorbent member.

The bandage permits the wound to be dressed while at the same time applying heat or cold, all in a single step. Therefore, a wounded patient can be tended to much quicker than with conventional methods which require the use of a separate wound dressing and hot/cold compress wrapping.

ALTERNATIVES

Figure 2:
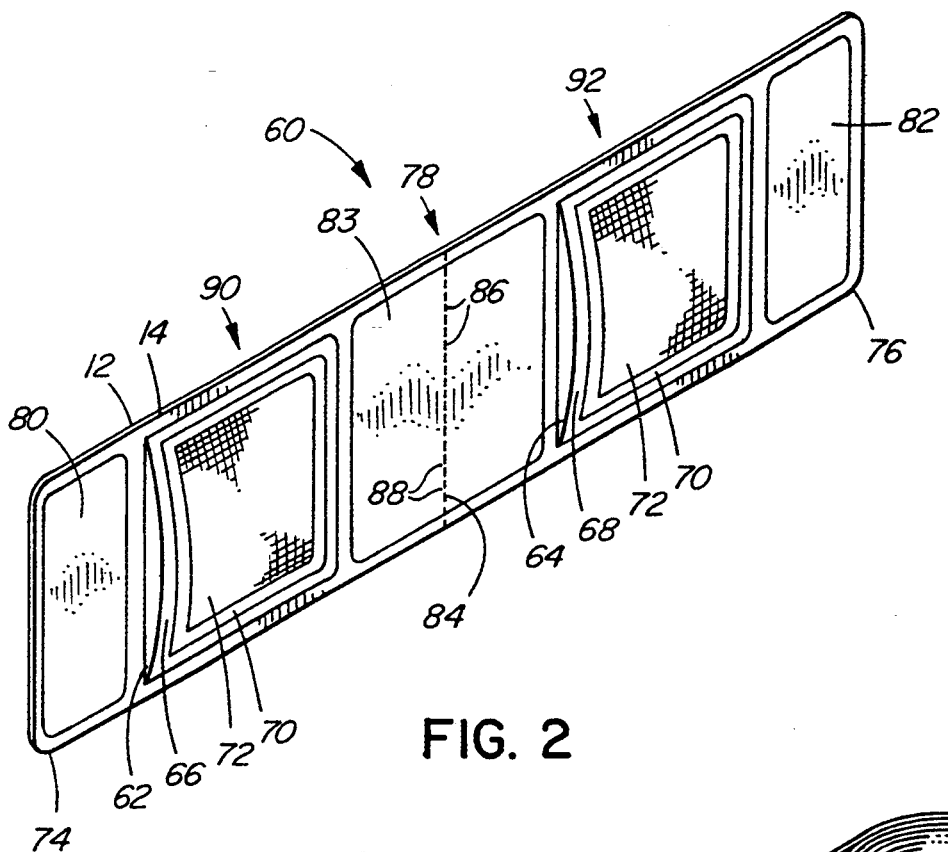
FIG. 2 is an oblique view of an apparatus according to a second embodiment of the invention.

Referring to FIG. 2, an apparatus according to a second embodiment of the invention is shown generally at 60. The apparatus includes first and second flexible members 12 and 14, similar to the flexible members described with respect to the first embodiment. The apparatus described in FIG. 2 however, includes first and second spaced apart slits 62 and 64 forming first and second pockets 66 and 68 respectively. To the outsides of respective pockets are secured respective moisture barrier sheets 70 and respective fluid absorbent members 72.

The apparatus has first and second end portions 74 and 76 and a mid portion 78. First and second adhesive portions 80 and 82 are secured to the first and second end portions respectively and a third adhesive portion 83 is secured to the mid portion 78.

The apparatus further has a perforation line 84 having a plurality of perforations 86 which extend through the first and second flexible members 12 and 14 and through the third adhesive portion 83. Thus a plurality of frangible portions 88 are formed between the perforations 86. The perforation line divides the apparatus into first and second separable units 90 and 92, separable at the perforation line 84.

In this embodiment, the third adhesive portion 83 is similar in shape to two of, say, the first adhesive portions 80 placed side by side and thus when the first and second units are separated, each unit has respective first and second adhesive portions which are the same size and thus each has the same holding capacity.

It has been found that if the overall length of the above apparatus is chosen such that the apparatus just wraps around a person's head, a convenient head bandage is formed. If the apparatus is provided in such lengths, units may conveniently be separated as required, to treat areas other than the head and further apparatuses can be left unseparated to treat the head. Consequently this configuration provides a bandage which is adaptable to the various requirements often presented for a bandage.

Figure 3:
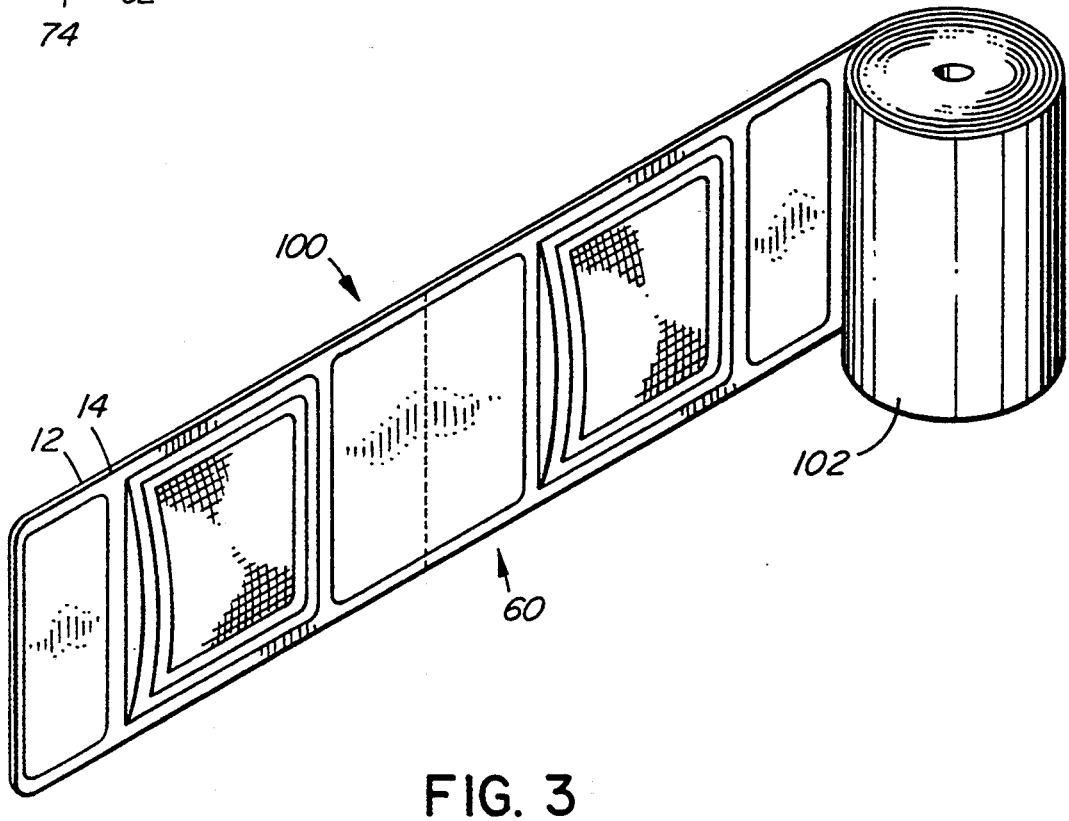
FIG. 3 is an oblique view of an apparatus according to a third embodiment of the invention.

Referring to FIG. 3, a third embodiment of the invention is shown generally at 100. In this embodiment, the double unit apparatus illustrated in FIG. 2 is repeated along a very long length of the first and second flexible sheets 12 and 14 such that the apparatus exists in the form of a roll 102 of double unit bandages 60. This configuration permits easy dispensing of the double unit bandages as the roll can be placed in a dispenser or may be held similar to a paper towel holder and the double unit bandages can merely be separated from the roll as desired. This has a particular advantage in an emergency setting where a patient can be treated quickly by simply tearing a double unit bandage from the roll, wrapping it around the patient and inserting a precooled or pre-heated gel pack or gel packs into the pockets in the double unit. This of course, is quicker than the conventional method of applying a dressing to the wound, then wrapping a gel pack holder around the dressing and then inserting a gel pack into the pocket.

ALTERNATIVE THERMAL MEDIA

Figure 4:
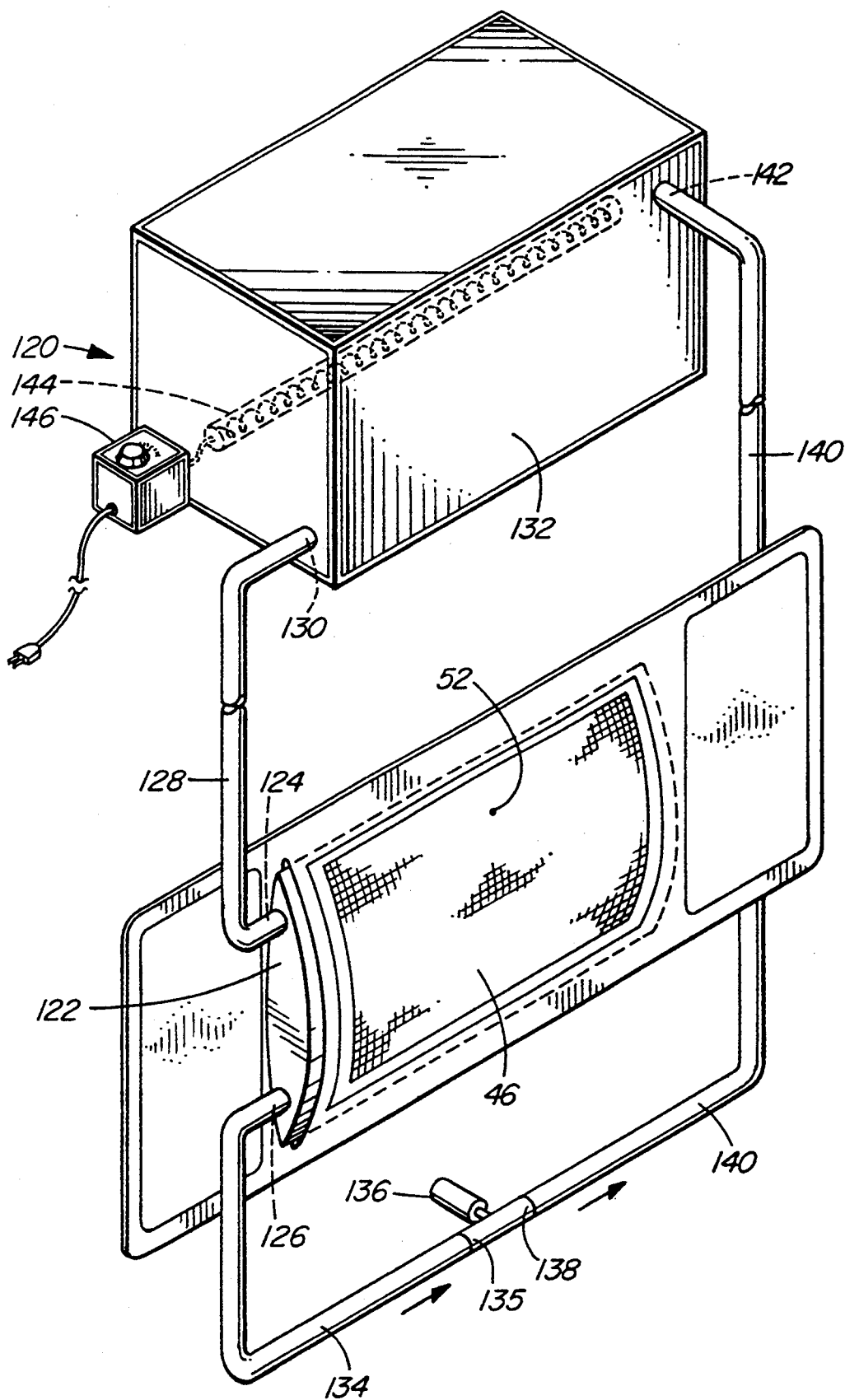
FIG. 4 is an oblique view of an apparatus according to the first embodiment employing a water circulating apparatus according to a fourth embodiment of the invention.

Referring to FIG. 4, an alternative apparatus for holding a thermal medium is shown generally at 120. The apparatus includes a water tight bag 122 having an inlet nipple 124 and an outlet nipple 126. To the inlet nipple is connected a first length of surgical tubing 128 leading to an outlet 130 of a water reservoir 132. To the outlet nipple 136 is connected a second length of surgical tubing 134 which is further connected to an inlet 135 of a waterpump 136. The waterpump also has an outlet 138 to which is connected a third length of surgical tubing 140 which is further connected to an inlet 142 of the reservoir 132.

Inside the reservoir 132, there is located a water heater 144 controlled by a thermostat 146. The thermostat allows a pre-determined water temperature to be selected and controls electric power to the water heater to heat water in the reservoir to the pre-determined water temperature and maintain the water at that temperature.

Preferably, the water reservoir is located higher than the bag 122 to produce a static head tending to create sufficient water pressure to create a flow of water from the reservoir, through the first surgical tubing 128 and into the bag. The water pump 136 further assists the static head in creating the flow of water by pumping water from the bag 122 back into the reservoir 132. In effect therefore water heated to the pre-determined temperature flows into the bag 122 where the heat in the water is transferred to the patient's wound through the wound contacting surface 52 of the fluid absorbent member 46. Thus the water in the bag is cooled due to this transfer of heat. The cooled water is conducted by the second surgical tubing 134 to the pump 136 which pumps the cooled water through the third surgical tubing 140, back into the reservoir 132. The cooled water entering the reservoir is reheated through contact with the water already in the reservoir and by the heater 144.

Alternatively, for applications where coldness on the wound is desirable the heater 144 may be replaced with a cooling coil of a refrigeration system (not shown) in which case the water in the reservoir would be cooled to a predetermined temperature and cooled water would be circulated into the bag 122 such that heat is drawn from the patient's wound through the fluid absorbent member 46 and the moisture barrier. The cooled water would then be conducted by the second surgical tubing 134 to the pump 136 to pump the heated water through the third surgical tubing 140, back into the reservoir 132. The heated water entering the reservoir would then be re-cooled through contact with the water already in the reservoir and by the cooling coil.

Alternatively, the reservoir may be fitted with both a heater and a cooling coil and provisions may be provided for selecting operation of either the heater or the cooling coil.

In another embodiment (not shown) the first surgical tubing may simply be connected to a conventional water tap and the associated hot and cold water valves may be regulated by hand until water at a pre-determined temperature is dispensed from the tap. The second surgical tubing may be routed from the bag to a conventional sink to permit water to flow out of the bag.

ALTERNATIVE BANDAGE CONFIGURATION

Figure 5:
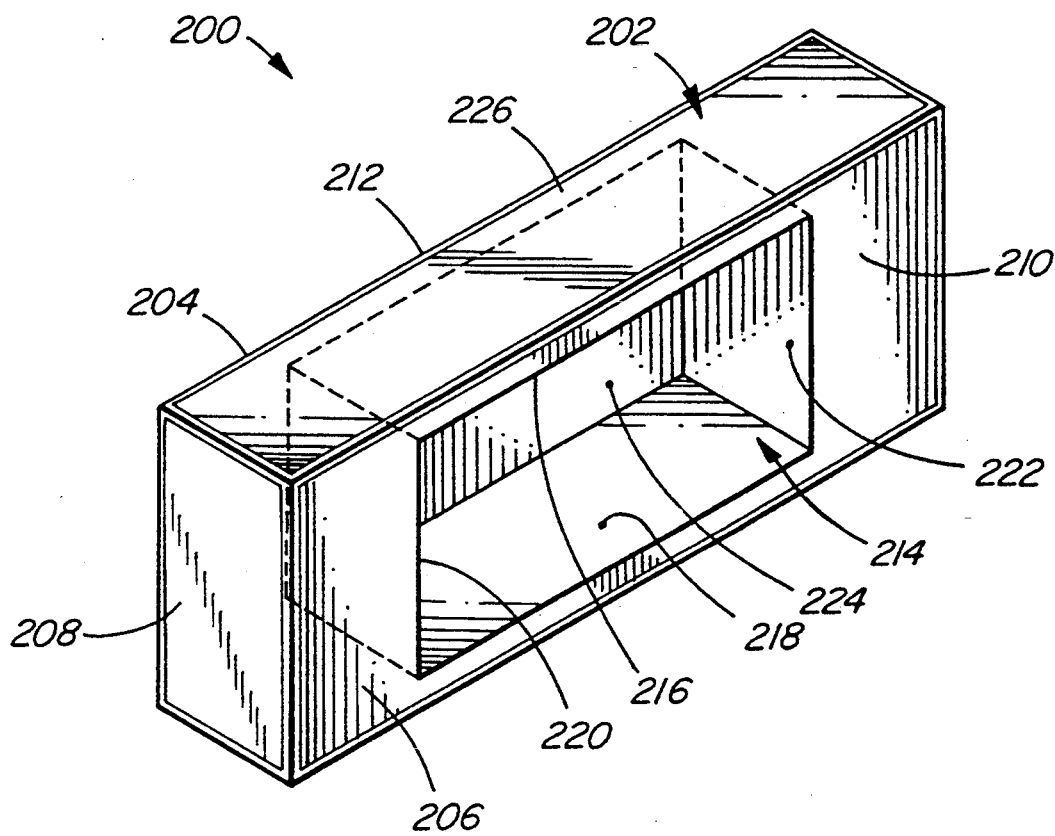
FIG. 5 is an oblique view of an apparatus according to a fifth embodiment of the invention.

Referring to FIG. 5, an alternative bandage apparatus is shown generally at 200. In this embodiment, the apparatus is formed from a conventional one-inch thick absorbent cotton pad 202.

The pad 202 has first and second opposite face sides 204 and 206 and first and second opposite end portions 208 and 210. The first face side 204 has a wound contacting surface 212 which extends from the first end portion 208 to the second end portion 210. The first and second opposite end portions 208 and 210 act to absorb fluids produced by an open wound in contact with the wound contacting surface. The second face side 206 has a square recess 214 cut therein for receiving a hot or cold medium (not shown). The recess acts as a pocket for holding a thermal medium.

The recess 214 has first, second, third, and fourth side walls 216, 218, 220, 222 and a bottom portion 224. The bottom portion 224 is separated from the wound contacting surface 212 by only a relatively small spacing portion 226 of fluid absorbent padding through which heat is transferred to or from the wound to or from a hot or cold medium in the recess 214.

In this embodiment the temperature medium may be a gel pack, a hot water bottle, the water bag described with reference to FIG. 4, a zip-lock bag containing water or the like. Any of these temperature media containers may be secured in the recess 214 using conventional adhesive tape placed over the recess after the container has been placed in the recess.

Figure 6:
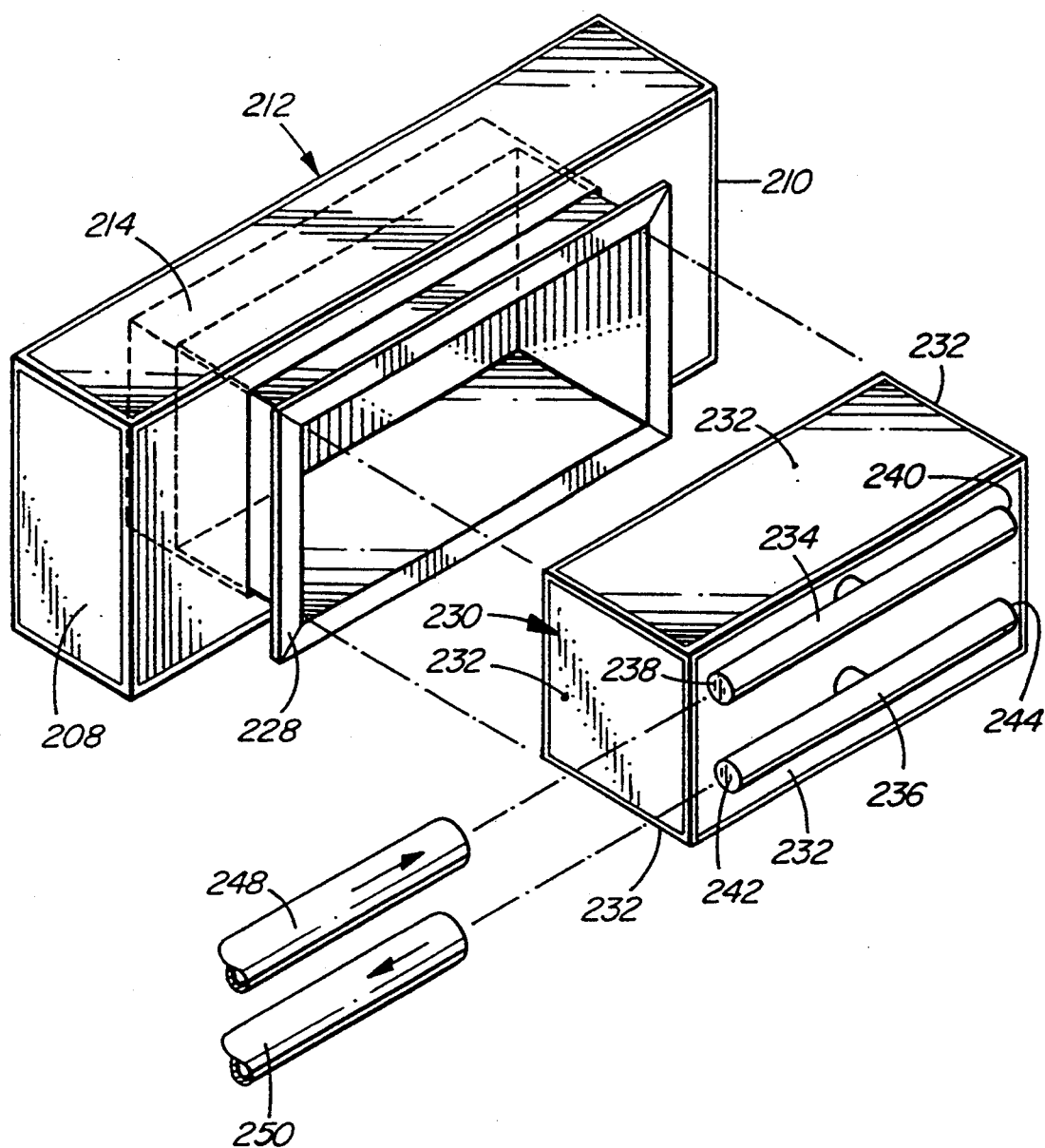
FIG. 6 is an oblique view of an apparatus according to a sixth embodiment of the invention.

Alternatively, referring to FIG. 6, a pre-formed shell insert 228 formed of a plastic material and having a shape similar to the recess 214 is placed into the recess. Preferably, the shell insert 228 has relatively thin walls to reduce any heat insulating properties of the plastic. Also preferably, the shell insert is water tight and therefore heated water or water with ice may be placed directly into the shell insert and a fluid impermeable tape(not shown) may be placed across the shell such that the water is prevented from escaping from the shell. The shell thus acts as a moisture barrier in this embodiment.

Alternatively, the temperature medium may be a gel pack, a hot water bottle, the water bag described with reference to FIG. 4, a zip-lock bag containing water or the like.

This embodiment also lends itself to the use of a rigid thermal media container such as that designated 230. This container includes six rigid sides 232 which completely enclose an inside space for holding water or other thermal medium. To one of the faces 232 are secured first and second "T" shaped conduits 234 and 236 respectively. The first conduit has respective first and second opposite openings 238 and 240 and the second conduit also has first and second opposite openings 242 and 244. Each opening is in communication with the inside space such that water can be forced into or extracted from the inside space via the openings 238-244.

The conduits 234 and 236 are round in shape and are therefore operable to connect to suitably sized first and second surgical tubing 248 and 250 which may be connected to the reservoir described in FIG. 4 for circulating water through the container 230.

If only one bandage 204 is used, then only one container 230 need be used. In this case the second openings 240 and 244 would be closed by an appropriate cap (not shown).If a plurality of bandages are used then a plurality of containers 230 may be used, wherein one container is associated with each bandage unit. In such an application, additional conduits of surgical tubing may be connected between the second openings 240 and 244 of a first container and first openings (238 and 242) of a second container. This effectively connects the containers in parallel such that each container receives water from the reservoir and thus each container contains water at the same temperature.

MATERIAL SELECTION

The first and second flexible sheets described with respect to the first, second and third embodiments may be formed from a variety of materials selected to suit the particular application. In particular, the first and second flexible members may be formed from a cotton yarn/Spandex (trademark) combination or from rubber thread. White crepe bandage devices may be manufactured using a polyester/rayon blend. Or, non woven products may be used such as spunbonded or meltblown polypropylene. A soft cloth-like feel may be provided in the bandage by employing Rayon (trademark), Spunlace (trademark) or Sontara(trademark). These materials tend to be more water proof and tend to "breathe" better than other materials.

A suitable material for the absorbent member is highly absorbent cotton as commonly used in tracheotomy and laparotomy sponges. Alternatively a plurality of layers may be used wherein such layers may include a nonwoven saffron microporous surface layer for instantly absorbing fluid and preventing them from seeping back to the wound. Behind the surface layer may be a layer of absorbent paper for liquid dispersal and behind this layer may be an embossed pad which contains a superabsorbent polymer to quickly draw and absorb liquid. A second layer of absorbent paper may be employed behind the superabsorbent polymer and a PE film leak proof wetness barrier may be employed behind the second layer of absorbent paper. This wetness barrier may take the place of the moisture barrier described with reference to the first embodiment.

While specific embodiments of the invention have been described and illustrated, such embodiments should be considered illustrative of the invention and not as limiting the invention as construed in accordance with the accompanying claims.

What is claimed is:

1. A thermal bandage apparatus for simultaneously dressing and thermally treating a wounded bodily area, the thermal bandage comprising:
   a) a fluid absorbent member having a wound contacting surface for absorbing bodily fluids produced by an open wound;
   b) securing means integral to the bandage, for securing the bandage in contact with the wound, the securing means including first and second flexible portions connected to and extending on opposite sides of the fluid absorbent member, the first and second flexible portions having first and second adhesive portions respectively, the first and second adhesive portions facing in the same direction as the wound contacting surface such that the adhesive portions adhere to areas adjacent to and on opposite sides of the wound;
   c) a pocket adjacent and connected to the fluid absorbent member for holding a thermal medium against the fluid absorbent member such that heat is transferred between the thermal medium and the open wound by thermal conduction through the fluid absorbent member; and
   d) pocket accessing means including an opening for accessing the pocket to permit replacement of the thermal medium without requiring that the fluid absorbent member be removed from the wound.

2. An apparatus as claimed in claim 1 wherein the pocket has a first side formed by said fluid absorbent member and a second side formed by a flexible sheet secured to said fluid absorbent member.

3. An apparatus as claimed in claim 2 wherein said fluid absorbent member includes a moisture barrier for preventing fluids from passing from the wound contacting surface to the pocket.

4. An apparatus as claimed in claim 2 wherein the fluid absorbent member has a wound facing side, the wound contacting surface being on the wound facing side, and wherein the fluid absorbent member has a pocket facing side opposite the wound facing side, and wherein the pocket includes a sheet of flexible material secured to the pocket facing side about its edges such that said pocket is formed between said pocket facing side and said sheet of flexible material.

5. An apparatus as claimed in claim 2 further including closure means for closing the opening to prevent a container installed therein from falling out of the pocket.

6. An apparatus as claimed in claim 5 wherein the closure means includes a flap for covering the opening.

7. An apparatus for treating a wound, the apparatus including:
   a) a fluid absorbent member having a wound contacting surface for absorbing bodily fluids produced by an open wound;
   b) securing means integral to the apparatus, for securing the bandage in contact with the wound, the securing means including first and second flexible portions connected to and extending on opposite sides of the fluid absorbent member, the first and second flexible portions having first and second adhesive portions respectively, the first and second adhesive portions facing in the same direction as the absorbent member such that the adhesive portions adhere to areas adjacent to and on opposite sides of the wound;
   c) a pocket adjacent and connected to the fluid absorbent member;
   d) pocket accessing means including an opening for accessing the pocket to permit access thereto when the fluid absorbent member is in contact with a wound;
   e) temperature gradient means in the pocket, for maintaining a temperature gradient through said fluid absorbent member, the temperature gradient means being held against the fluid absorbent member such that heat is transferred between the temperature gradient means and the open wound by thermal conduction through the fluid absorbent member, the temperature gradient means being operable to be replaced in the pocket without requiring that the fluid absorbent member be removed from the wound.

8. An apparatus as claimed in claim 7 wherein said temperature gradient means includes a container for containing a thermal medium.

9. An apparatus as claimed in claim 8 wherein said thermal medium includes a gel material.

10. An apparatus as claimed in claim 8 wherein said thermal medium includes water.

11. An apparatus as claimed in claim 7 wherein said fluid absorbent member includes a moisture barrier for preventing fluids from passing from the wound contacting surface to the thermal medium.

12. An apparatus as claimed in claim 7 wherein the fluid absorbent member has a wound facing side, the wound contacting surface being on the wound facing side, and wherein the fluid absorbent member has a pocket facing side opposite the wound facing side, and wherein the pocket includes a sheet of flexible material secured to the pocket facing side about its edges such that said pocket is formed between said pocket facing side and said sheet of flexible material.

13. An apparatus as claimed in claim 8 further including closure means for closing the opening to prevent the container from falling out of the pocket.

14. An apparatus as claimed in claim 13 wherein the closure means includes a flap for covering the opening.

15. A thermal bandage apparatus for simultaneously dressing and thermally treating a wounded bodily area, the thermal bandage comprising:
   a) a fluid absorbent member having a wound contacting surface for absorbing bodily fluids produced by an open wound;
   b) first and second flexible members, at least one of which is connected to the fluid absorbent member, the first and second flexible members having respective perimeter portions joined together such that said first and second flexible members are parallel to each other and such that a pocket is formed between said first and second flexible members, said pocket being adjacent to the fluid absorbent member and being operable to hold a thermal medium against the fluid absorbent member such that heat is transferred between the thermal medium and said wounded bodily area through the fluid absorbent member;
   c) pocket accessing means including an opening in at least one of said first and second flexible members for accessing the pocket; and
   d) securing means on at least one of said first and second flexible members, for securing the bandage in contact with the wound, said securing means including first and second flexible portions extending on opposite sides of the fluid absorbent member, the first and second flexible portions having first and second adhesive portions respectively.

* * * * *